US009295815B2

(12) United States Patent
Stevens et al.

(10) Patent No.: US 9,295,815 B2
(45) Date of Patent: Mar. 29, 2016

(54) TORQUER DEVICE AND METHODS RELATED THERETO

(71) Applicant: Merit Medical Systems, Inc., South Jordan, UT (US)

(72) Inventors: Brian Stevens, Plesant Grove, UT (US); Gregg Stuart Sutton, Maple Grove, MN (US); Eric Joseph Dille, Eden Prairie, MN (US)

(73) Assignee: Merit Medical Systems, Inc., South Jordan, UT (US)

( * ) Notice: Subject to any disclaimer, the term of this patent is extended or adjusted under 35 U.S.C. 154(b) by 173 days.

(21) Appl. No.: 13/890,861

(22) Filed: May 9, 2013

(65) Prior Publication Data

US 2013/0303330 A1 Nov. 14, 2013

Related U.S. Application Data

(60) Provisional application No. 61/644,790, filed on May 9, 2012.

(51) Int. Cl.
| | |
|---|---|
| *F16H 1/46* | (2006.01) |
| *A61B 17/16* | (2006.01) |
| *A61B 19/00* | (2006.01) |
| *A61M 25/09* | (2006.01) |
| *A61M 25/01* | (2006.01) |
| *A61B 17/00* | (2006.01) |

(52) U.S. Cl.
CPC ..... *A61M 25/09041* (2013.01); *A61M 25/0113* (2013.01); *A61B 17/1622* (2013.01); *A61B 17/1624* (2013.01); *A61B 19/30* (2013.01); *A61B 2017/00469* (2013.01); *A61M 25/013* (2013.01); *A61M 2025/09116* (2013.01); *F16H 1/46* (2013.01)

(58) Field of Classification Search
CPC .......... A61B 17/1622; A61B 17/1624; A61B 18/1492; A61B 19/30; F16H 1/46
See application file for complete search history.

(56) References Cited

U.S. PATENT DOCUMENTS

| | | | |
|---|---|---|---|
| 5,392,778 A | 2/1995 | Horzewski | |
| 5,569,034 A | 10/1996 | Meller et al. | |
| 5,975,900 A | 11/1999 | Garman | |
| 5,993,454 A * | 11/1999 | Longo | 606/80 |
| 7,972,282 B2 | 7/2011 | Clark et al. | |
| 8,696,511 B2 * | 4/2014 | Steele et al. | 475/254 |
| 2004/0010258 A1 | 1/2004 | Carusillo et al. | |
| 2006/0121412 A1* | 6/2006 | Kuhn | 433/105 |
| 2006/0252595 A1* | 11/2006 | Koseki | 475/331 |

(Continued)

FOREIGN PATENT DOCUMENTS

| | | |
|---|---|---|
| WO | WO93/18817 | 9/1993 |
| WO | 2004047664 | 6/2004 |
| WO | WO 2013143563 A1 * | 10/2013 |

OTHER PUBLICATIONS

International Search Report and Written Opinion dated Aug. 12, 2013 for PCT/US2013040391.

(Continued)

*Primary Examiner* — Tisha Lewis
(74) *Attorney, Agent, or Firm* — Stoel Rives LLP

(57) ABSTRACT

Torque devices are disclosed for controlling insertion of medical devices into a lumen of a patient. The torque devices allow for modulation of the speed of rotation of the medical devices. Methods related to the torque devices are also disclosed.

23 Claims, 3 Drawing Sheets

(56) References Cited

U.S. PATENT DOCUMENTS

| | | |
|---|---|---|
| 2009/0124934 A1 | 5/2009 | Rabbitte et al. |
| 2009/0287203 A1* | 11/2009 | Mazzone et al. ................ 606/21 |
| 2011/0264074 A1 | 10/2011 | Tegg et al. |
| 2015/0148176 A1* | 5/2015 | Schroeder et al. .............. 606/21 |

OTHER PUBLICATIONS

European Search Report dated Dec. 16, 2015 for EP13788377.5.

* cited by examiner

TORQUER DEVICE AND METHODS RELATED THERETO

CROSS-REFERENCE TO RELATED APPLICATIONS

Under 35 U.S.C. §119(e), this application claims the benefit of U.S. Provisional Patent Application No. 61/644,790, entitled "TORQUER DEVICE," filed May 9, 2012, the contents of which are hereby incorporated herein by reference in their entirety.

TECHNICAL FIELD

The present disclosure relates generally to medical devices. More specifically, the present disclosure relates to medical devices capable of insertion into a lumen of a patient, such as catheters and guidewires. Even more specifically, the present disclosure relates to torque devices for controlling insertion of medical devices into a patient and methods related to the torque devices.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings are not necessarily drawn to scale unless specifically indicated. These drawings depict only typical embodiments, which will be described with additional specificity and detail through use of the accompanying drawings in which:

DETAILED DESCRIPTION

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments.

Medical apparatuses may be deployed in various body lumens for a variety of purposes. Guidewires may be deployed, for example, throughout the vascular system to guide the placement or removal of catheters and other medical apparatuses. At times it is desired to rotate a medical apparatus to assist in penetrating or clearing an occlusion in a blood vessel or other body lumen. For example, in rotational atherectomy, microscopic blades or teeth are rotated to break up occlusions.

For convenience, many of the specific examples included below reference guidewires and/or catheters. Notwithstanding any of the particular medical apparatuses referenced in the examples or disclosure below, the disclosure and examples may apply analogously to any medical apparatus where rotation of that medical apparatus is desired.

The phrases "operably connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations. For example, the proximal end of a torque device is defined as the end closest to the user during operation of the torque device. The distal end is the end opposite the proximal end, along the longitudinal direction of the torque device.

Figure 1:
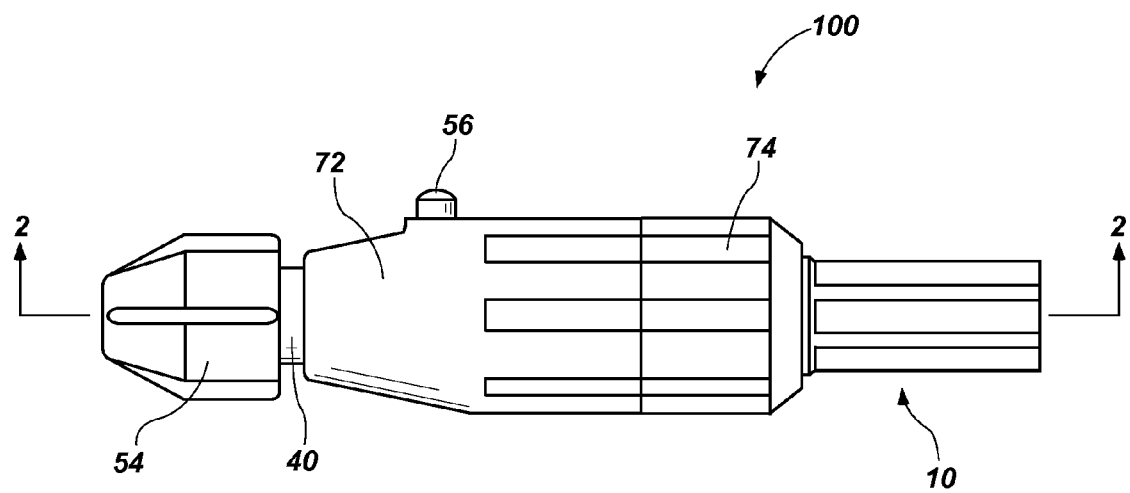
FIG. 1 is a side view of one embodiment of a torque device.
Figure 2:
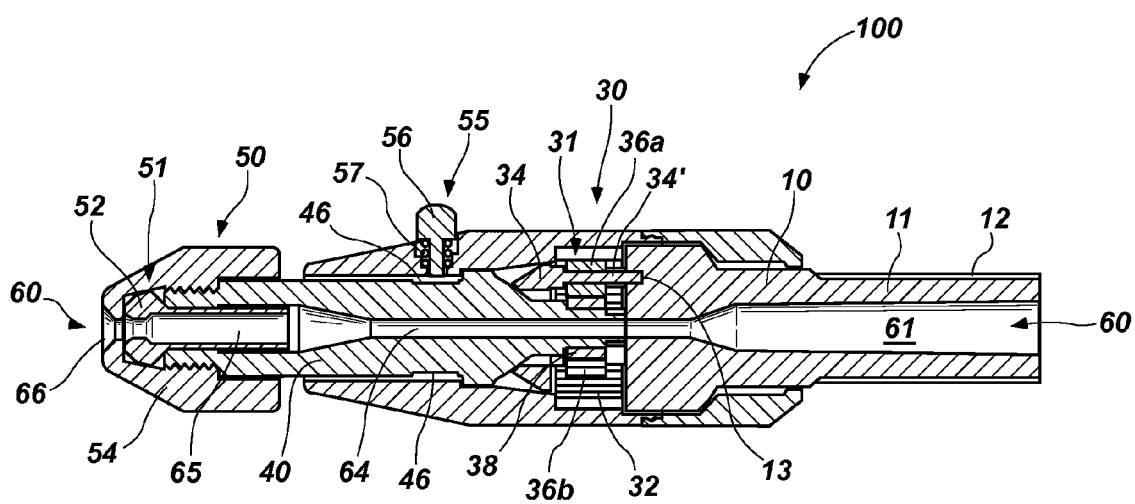
FIG. 2 is a cross-sectional view along the line 2-2 of the torque device illustrated in FIG. 1.
Figure 3:
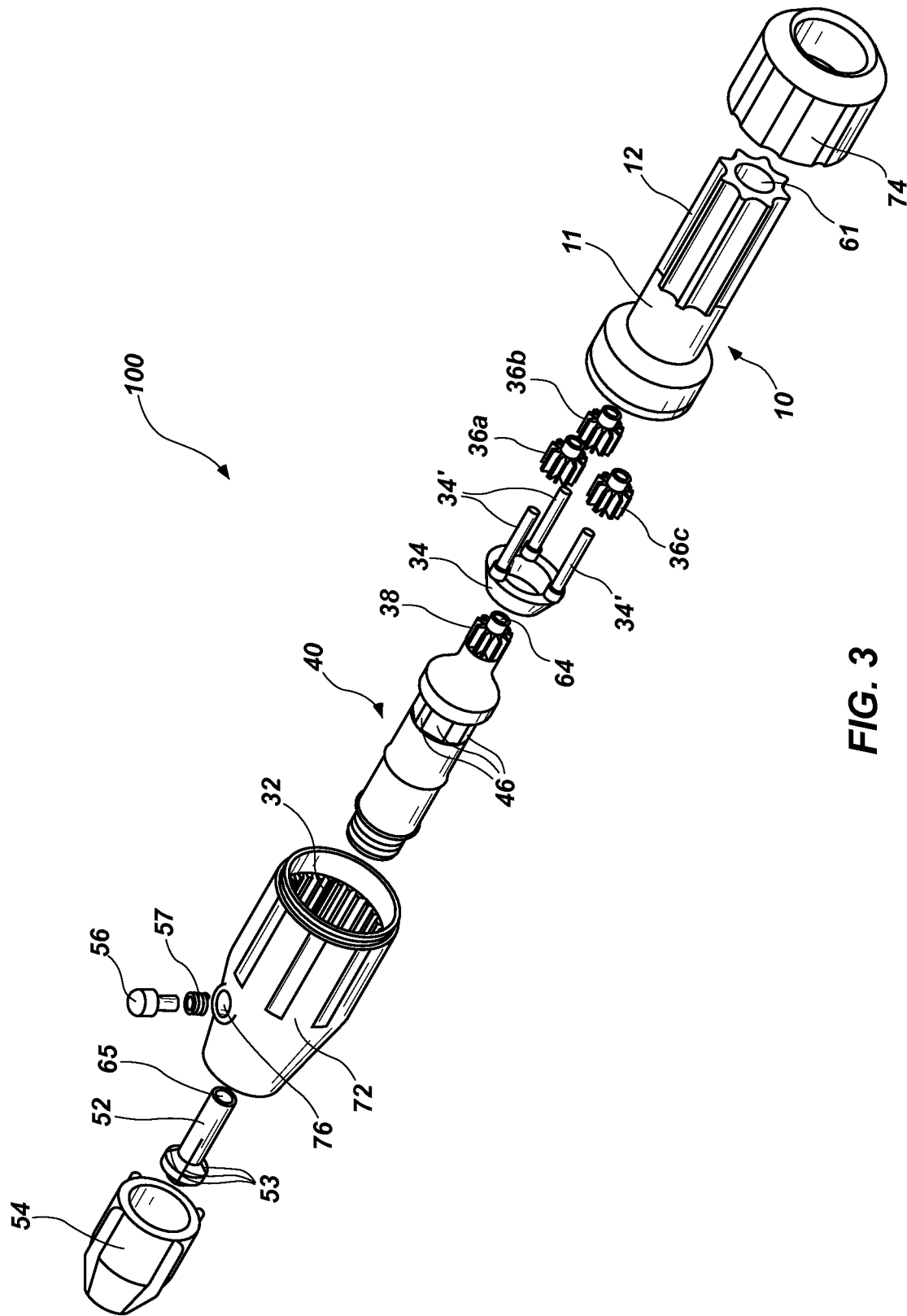
FIG. 3 is an exploded perspective view of the torque device illustrated in FIG. 1.

FIGS. 1-3 illustrate one embodiment of a torque device 100. Torque device 100 comprises a torque input member 10. Torque device 100 further comprises a speed modulating system 30 operably connected to the torque input member 10. Torque device 100 further comprises a clamp system 50 configured to securely and releasably engage a medical apparatus. The clamp system 50 is operably connected to the speed modulating system 30. Rotation of the torque input member 10 results in rotation of the clamp system 50 at a modulated rate relative to the rotation of the torque input member 10.

In the illustrated embodiment the speed modulating system 30 is configured to increase the rotational speed of the clamp system 50 relative to the rotational speed of the torque input member 10. Alternatively, the speed modulating system 30 may be configured to decrease the rotational speed of the clamp system 50 relative to the rotational speed of the torque input member 10.

In the illustrated embodiment, the torque input member 10 is configured for rotation by a single person and is configured for manual rotation with one hand. The torque input member 10 comprises a shank 11 configured to allow a user to grasp the torque input member 10. The shank 11 comprises a grippable surface 12.

Alternatively, rather than being configured for hand-driven rotation, the torque device 100 may further comprise an actuator (not shown) operably connected to the torque input member 10. For example, the actuator may comprise an electric motor or a pneumatic drive.

In the illustrated embodiment, the speed modulating system 30 comprises a planetary gear system 31. The planetary gear system 31 comprises a ring gear 32, a planet carrier 34, a first planet gear 36a, a second planet gear 36b, a third planet gear 36c, and a sun gear 38. The planetary gear system 31, in the illustrated embodiment, is configured to increase the rotational speed of the clamp system 50 relative to the rotational speed of the torque input member 10. For example, the planetary gear system 31 may be configured to increase the rotational speed of the clamp system 50 relative to the rotational speed of the torque input member 10 by at least about two times, by at least about three times, by at least about four times, by at least about five times, by at least about six times, by at least about seven times, by at least about eight times, by at least about nine times, by at least about ten times, by at least about eleven times, and/or by at least about twelve times.

First planet gear 36a, second planet gear 36b, and third planet gear 36c are each rotatably mounted on the planet carrier 34. The planet carrier 34 is fixedly engaged with the torque input member 10 and is configured to rotate with the torque input member 10. First planet gear 36a, second planet gear 36b, and third planet gear 36c are each rotatably mounted on a separate prong 34' of the planet carrier 34. Each prong 34' inserts into a corresponding receptacle 13 formed in torque input member 10. The interaction between each of the three prongs 34' and each of the three receptacles 13 fixes the rotation of the planet carrier 34 to the rotation of the torque input member 10.

In the illustrated embodiment, there are three planet gears. Alternatively, there may be the first planet gear 36a, only the first planet gear 36a and the second planet gear 36b, or more than three planet gears with a corresponding number of prongs 34' depending upon the number of planet gears.

In the illustrated embodiment, the ring gear 32, the planet carrier 34, and the sun gear 38 are each coaxial.

In the illustrated embodiment, the ring gear 32 is fixedly mounted to the inner surface of a distal housing 72 of the torque device 100. First planet gear 36a, second planet gear 36b, and third planet gear 36c are each configured to rotate within and engage with the ring gear 32. The sun gear 38 is fixedly mounted to an output shaft 40. The sun gear 38 is configured for rotation by first planet gear 36a, second planet gear 36b, and third planet gear 36c. In the illustrated embodiment, output shaft 40 provides a bearing surface for the rotation of planet carrier 34. Alternatively, other bearing arrangements may be utilized for the free rotation of planet carrier 34 and output shaft 40. Ring gear 32, first planet gear 36a, second planet gear 36b, third planet gear 36c, and sun gear 38 may be of any diameter and have any number of teeth compatible with the desired gear ratio.

In the illustrated embodiment, the output shaft 40 is operably connected to the clamp system 50. Rotation of the output shaft 40 results in rotation of the clamp system 50. Accordingly, rotation of the output shaft 40 also rotates the medical apparatus secured by the clamp system 50. Thus, rotation of the torque input member 10 at a first speed results in rotation of the medical apparatus secured by the clamp system 50 at a second speed, wherein the second speed is determined by gear ratios of the speed modulating system 30.

The planetary gear system 31 may be configured to reduce the rotational speed of the clamp system 50 relative to the rotational speed of the torque input member 10. For example, the planetary gear system 31 may be configured to reduce the rotational speed of the clamp system 50 relative to the rotational speed of the torque input member 10 by at least about 10%, by at least about 20%, by at least about 25%, by at least about 30%, by at least about 33%, by at least about 40%, by at least about 45%, by at least about 50%, by at least about 55%, by at least about 60%, by at least about 66%, by at least about 70%, by at least about 75%, by at least about 80%, by at least about 85%, and/or by at least about 90%.

Also, torque device 100 may be configured for selection of increased or reduced rotational speed of the clamp system 50 relative to the rotational speed of the torque input member 10. In that embodiment, speed modulating system 30 may be configured to operate in either a reduction gear mode or an increasing gear mode.

In the illustrated embodiment, the clamp system 50 comprises a chuck 51. The chuck 51 comprises a collet 52. The collet 52 comprises four kerfs 53 (three of which are visible in FIG. 3) in the sidewall of the collet 52 at the distal end of the collet 52. The clamp system 50 further comprises a collar 54 configured for operable engagement with the collet 52 and configured to compress the kerfs 53 of the collet 52 and thereby reduce the inner diameter of the collet 52. The reduction in diameter of the collet 52 is what allows clamp system 50 to securely engage a cylindrically-shaped medical apparatus, such as a guidewire or catheter. The collar 54 and the collet 52 each comprises corresponding tapered surfaces configured to engage with each other and thereby compress the kerfs 53 of the collet 52 depending upon the amount of engagement between the tapered surfaces.

The collar 54 is configured for threaded engagement with output shaft 40. The amount of threaded engagement between the collar 54 and the output shaft 40 determines the amount of engagement between the tapered surfaces of the collar 54 and the collet 52. Accordingly, the amount of threaded engagement between the collar 54 and the output shaft 40 determines the reduction in diameter of the collet 52 and, therefore, the amount of pressure on the medical apparatus, such as a guidewire or catheter.

In some embodiments, the chuck 51 comprises a keyless chuck. The chuck 51 may also comprise a keyed chuck. The chuck 51 may also comprise a self-centering chuck.

As disclosed previously, in the illustrated embodiment, torque device 100 comprises the distal housing 72. The ring gear 32 is fixedly mounted to the inner surface of a distal housing 72. Proximal housing 74 is configured to threadedly engage distal housing 72. Proximal housing 74 is configured to hold torque input member 10 in place, which thereby holds the planet carrier 34, first planet gear 36a, second planet gear 36b, and third planet gear 36c in place. Proximal housing 74 also provides bearing surfaces for the rotation of torque input member 10 within the annulus of proximal housing 74.

In some embodiments, distal housing 72 and/or proximal housing 74 are not present. Other methods and members for operably connecting torque input member 10 with speed modulating system 30 may be used.

In the illustrated embodiment, the clamp system 50 further comprises a lock system 55 configured to prevent rotation of the speed modulating system 30 and/or the torque input member 10 during engagement and disengagement of the chuck 51 with a medical apparatus. The output shaft 40 is configured to engage with a lock system 55 of the clamp system 50, wherein rotation of the output shaft 40 is resisted and/or prevented by the lock system 55. The output shaft 40 comprises a band of flattened regions 46.

Clamp system 50 further comprises a button 56 with a shank extending from the underside of the head of button 56. Button 56 resides in a receptacle 76 of distal housing 72. A cylindrical spring 57 sits within receptacle 76. The shank of button 56 fits within the interior of the cylindrical spring 57. When button 56 is depressed, cylindrical spring 57 is compressed and the bottom of the shank of button 56 contacts a flattened region 46 of output shaft 40. When button 56 is depressed with sufficient force, output shaft 40 is unable to rotate.

With button 56 depressed, a user can then thread on or unthread off collar 54 without rotating output shaft 40. Thus, with button 56 depressed a user can secure or release the medical apparatus from collet 52. Likewise, with button 56 depressed, a user can maneuver torque device 100 to maneuver or steer a medical apparatus within a lumen of a patient without rotating the medical apparatus within the torque device 100. When button 56 is released, spring 57 uncompresses and pulls the shank of button 56 out of contact with the flattened region 46 previously contacted. With button 56 released, a user can rotate output shaft 40. If the medical apparatus is secured by clamp system 50, then with button 56 released, a user may rotate the medical apparatus within a lumen of a patient by rotating torque input member 10.

In other embodiments, lock system 55 may be configured to have a selectable lock position such that a user would not have to continually depress a button 56 to secure and release the medical apparatus or to maneuver a medical apparatus within a lumen of a patient without rotating the medical apparatus.

For example, receptacle 76 may be an elongated groove extending longitudinally along the surface of distal housing 72 and opening into the interior of housing 72. The shank of button 56 may extend into the opening of housing 72. Spring 57 may not be present. Output shaft 40 may have an elongated groove extending longitudinally along the surface of output shaft 40. The elongated groove in the surface of output shaft 40 may be configured to mate with the shank of button 56. When button 56 is in a first position in receptacle 76 (such as at a proximal end thereof), the shank of button 56 may not engage the elongated groove of output shaft 40. Thus, in the first position, button 56 would not interfere with rotation of output shaft 40. However, when the elongated groove of output shaft 40 is aligned with the elongated groove of receptacle 76, button 56 may be slid to a second position in receptacle 76 (such as at a distal end thereof). The shank of button 56 would then be engaged within the groove of output shaft 40. Rotation of output shaft 40 would then be restricted by the shank of button 56. Accordingly, a user would be able to select between a first position where output shaft 40 is not locked and a second position where output shaft 40 is locked.

The foregoing example is just one example of how lock system 55 may be configured to have a selectable lock position. Numerous other methods of selectably locking the rotation of a shaft to a stationary member are known in the art and may be used with the torque device 100 to provide a selectable lock position with the aid of the present disclosure.

In the illustrated embodiment, the torque input member 10, the speed modulating system 30, and the clamp system 50 are each coaxial. Alternatively, the torque input member 10 may be offset from the clamp system 50. In that embodiment, the torque input member 10 and the clamp system 50 may be axially parallel. Instead of a planetary gear system, the torque input member 10 may be operably connected to a gear which is mated with a pinion operably connected with the output shaft 40. In another alternative, torque input member 10 may be operably connected to the output shaft 40 via a belt drive system.

In the illustrated embodiment, torque device 100 comprises a lumen 60 that runs the entire length of torque device 100 along the axial centerline. Lumen 60 is configured to allow the cylindrically-shaped medical apparatus to travel through the axial center of torque device 100. For example, a guidewire or catheter may be inserted through the lumen 60. The guidewire or catheter may then be inserted into a lumen in the body of a patient. When detailed guidance or rotation of the guidewire or catheter is necessary, clamp system 50 may then be secured to the appropriate length of the guidewire or catheter and the guidewire or catheter manipulated or rotated by the torque device 100.

Lumen 60 comprises lumen 61 that runs the entire length of torque input member 10, lumen 64 that runs the entire length of output shaft 40 and sun gear 38, and lumen 65 that runs the entire length of collet 52. Lumen 60 also comprises opening 66 in the distal end of collar 54. It should be understood that lumen 65 of collet 52 is created by the sidewall of collet 52. Thus, the diameter of lumen 65 is decreased when the kerfs 53 of collet 52 are compressed by collar 54, as discussed previously.

In other embodiments, to the extent that components of torque device 100 are not coaxial, then all of lumen 60 may not be present. For example, if torque input member 10 is not coaxial with output shaft 40, then lumen 61 may not be present. In that example, lumen 60 may still include lumens 64 and 65 and opening 66. In that example, a guidewire would only extend centrally through clamp system 50 and output shaft 40. Likewise, if output shaft 40 is not coaxial with collet 52, then lumen 64 would not be present. In such an embodiment, lumen 60 may only include lumen 65 and opening 66. In that embodiment, a guidewire would only extend through clamp system 50.

The torque device 100 may comprise an indicator that may be aligned with a selected portion of a medical apparatus. The indicator may be configured to indicate the rotational position of the selected portion of the medical apparatus. Thus, as the selected portion of the medical apparatus is rotated within the body of a patient, the indicator would allow a user to know the rotational position of the selected portion aligned with the indicator. For example, where the medical apparatus is a guidewire with a bend or hook at the end of the guidewire, the bend or hook may be aligned with the indicator, the guidewire may then be secured to the clamp system 50, and the guidewire inserted into a lumen in the body of a patient. As the guidewire is rotated by torque device 100, the indicator would identify the rotational position of the bend or hook. Thus, even if the guidewire is rapidly rotated to break through an occlusion, after the occlusion has been passed, a user would be able to look at the indicator and determine the rotational position of the bend or hook.

In one embodiment, the output shaft 40 may comprise an indicator that may be aligned with a selected portion of a medical apparatus, wherein the rotational position of the indicator indicates the rotational position of the selected portion of the medical apparatus. The indicator may comprise a symbol on the outer surface of the output shaft. Distal housing 72 may include windows to allow a user to see the rotational position of the indicator.

In the illustrated embodiment, torque input member 10 may be rotated either clockwise or counter-clockwise. Therefore, a medical apparatus may be rotated either clockwise or counter-clockwise by torque device 100. Alternatively, torque device 100 may be configured to only allow rotation in one direction. For example, torque device 100 may comprise detents configured to only allow rotation in one direction. The detents could be operably connected to any of the rotating components of the torque device 100, such as the torque input member 10, components of the speed modulating system 30, output shaft 40, and/or clamp system 50.

The torque device 100 may be made from any material or materials compatible with its intended use, such as, by way of non-limiting example, metals, such as aluminum and stainless steel; plastics, such as polyethylene, polypropylene, polystyrene, polyvinyl chloride, polycarbonate, and nylon; and composite materials. The various components of torque device 100 may be made of different materials. For example, collet 52 may be made of bronze or brass and the remainder of torque device 100 made of plastic. Additionally, ring gear 32, first planet gear 36a, second planet gear 36b, third planet gear 36c, and sun gear 38 may be made of a tough resilient plastic and the remainder of torque device 100 made of a less resilient or tough plastic.

In some embodiments, the clamp system 50 is configured to securely and releasably engage a guidewire. The guidewire may comprise at least one bend. The guidewire may comprise at least one cutting element. In some embodiments, the clamp system 50 is configured to securely and releasably engage a catheter. In some embodiments, the clamp system 50 is configured to securely and releasably engage a surgical drill bit.

Figure 4:
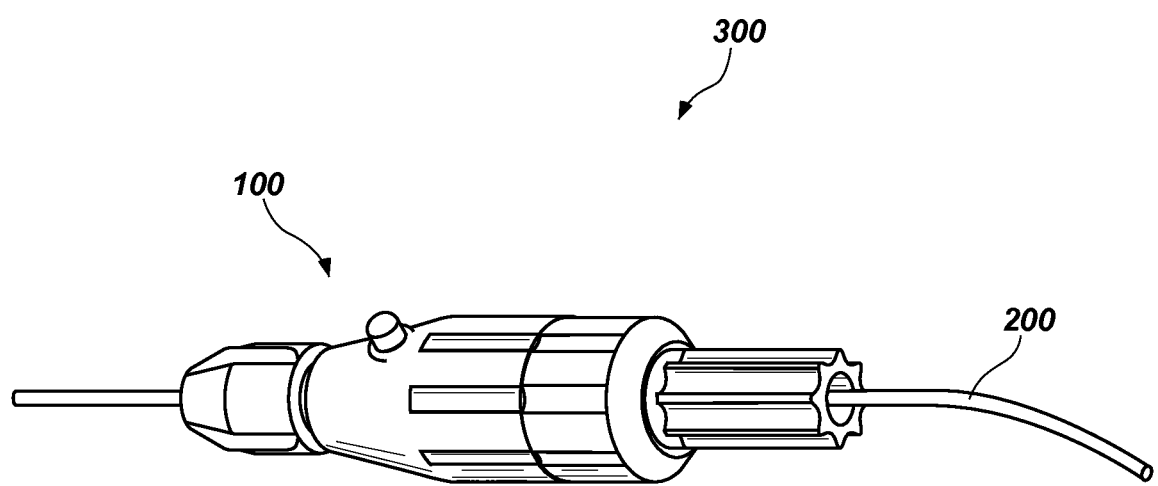
FIG. 4 is a perspective view of one embodiment of an assembled kit comprising the torque device of FIG. 1 and one embodiment of a medical apparatus.

A kit is also disclosed herein. The kit 300 comprises the torque device 100 and a medical apparatus 200. The medical apparatus 200 may be supplied separate from the torque device 100, but in the same package. FIG. 4 illustrates a perspective view of one embodiment of an assembled kit 300, where the medical apparatus 200 comprises a guidewire.

In some embodiments, the medical apparatus 200 comprises a guidewire. The guidewire may comprise at least one bend. The guidewire may comprise at least one cutting element. The guidewire may also include other medical apparatuses known in the art and used with guidewires. In some embodiments, the medical apparatus 200 comprises a catheter. In other embodiments, the medical apparatus 200 comprises a drill bit.

Methods of manipulating a medical apparatus are also disclosed herein. In one embodiment, a method of manipulating a medical apparatus comprises inserting a medical apparatus into a lumen of a patient's body. The method further comprises securing torque device 100 to the medical apparatus. The method further comprises rotating the torque input member 10 to thereby rotate the medical apparatus at a modulated speed.

In some embodiments of the methods, the torque device is configured to increase the rotational speed of the medical apparatus relative to the rotational speed of the torque input member. In other embodiments of the methods, the torque device is configured to decrease the rotational speed of the medical apparatus relative to the rotational speed of the torque input member.

In some embodiments, the methods further comprise locking the position of the clamp system when movement of the medical apparatus is desired without modulation of the rotational rate of the medical apparatus.

In some embodiments, the methods further comprise aligning a selected portion of the medical apparatus with an indicator of the torque device. Such methods may further comprise identifying a rotational position of the selected portion of the medical apparatus by viewing the indicator of the torque device.

While specific embodiments of torque devices and other medical appliances have been illustrated and described, it is to be understood that the disclosure provided is not limited to the precise configuration and components disclosed. Various modifications, changes, and variations apparent to those of skill in the art having the benefit of this disclosure may be made in the arrangement, operation, and details of the devices, methods, and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A torque device comprising:
    a torque input member defining a longitudinal axis and extending from the torque device such that the torque input member is directly graspable by a user such that the user can rotate the torque input member about its longitudinal axis;
    a speed modulating system operably connected to the torque input member;
    a clamp system configured to securely and releasably engage a medical apparatus, wherein the clamp system is operably connected to the speed modulating system; and
    wherein rotation of the torque input member results in rotation of the clamp system at a modulated rate relative to the rotation of the torque input member.

2. The torque device of claim 1, wherein the torque input member is configured for rotation by a single person.

3. The torque device of claim 1, wherein the speed modulating system is configured to increase the rotational speed of the clamp system relative to the rotational speed of the torque input member.

4. The torque device of claim 1, wherein the speed modulating system is configured to decrease the rotational speed of the clamp system relative to the rotational speed of the torque input member.

5. The torque device of claim 1, wherein the speed modulating system comprises a planetary gear system.

6. The torque device of claim 5, wherein the planetary gear system comprises a ring gear, a planet carrier, a planet gear, and a sun gear.

7. The torque device of claim 6, wherein the planetary gear system is configured to increase the rotational speed of the clamp system relative to the rotational speed of the torque input member.

8. The torque device of claim 6, wherein the planetary gear system is configured for selection of increased or reduced rotational speed of the clamp system relative to the rotational speed of the torque input member.

9. The torque device of claim 6, wherein the planet gear is rotatably mounted on the planet carrier, wherein the planet carrier is fixedly engaged with the torque input member and is configured to rotate with the torque input member.

10. The torque device of claim 6, wherein the ring gear, the sun gear, and the planet carrier are each coaxial.

11. The torque device of claim 6, wherein the ring gear is fixedly mounted to a housing of the torque device and wherein the planet gear is configured to rotate within and engage with the ring gear.

12. The torque device of claim 6, wherein the sun gear is fixedly mounted to an output shaft and wherein the sun gear is configured for rotation by the planet gear.

13. The torque device of claim 12, wherein the output shaft is operably connected to the clamp system, wherein rotation of the output shaft results in rotation of the clamp system and also rotation of any medical apparatus secured thereby.

14. The torque device of claim 1, further comprising an indicator configured to be aligned with a selected portion of the medical apparatus, wherein the indicator is configured to indicate the rotational position of the selected portion of the medical apparatus.

15. The torque device of claim 1, wherein the clamp system comprises a chuck.

16. The torque device of claim 15, wherein the chuck comprises a collet.

17. The torque device of claim 1, further comprising a lock system configured to prevent rotation of the speed modulating system and/or torque input member.

18. A kit comprising a torque device and a medical apparatus, wherein the torque device comprises:
    a torque input member defining a longitudinal axis and extending from the torque device such that the torque input member is directly graspable by a user such that the user can rotate the torque input member about its longitudinal axis;
    a speed modulating system operably connected to the torque input member;

a clamp system configured to securely and releasably engage the medical apparatus, wherein the clamp system is operably connected to the speed modulating system; and wherein rotation of the torque input member results in rotation of the clamp system at a modulated rate relative to the rotation of the torque input member.

19. The kit of claim 18, wherein the medical apparatus comprises a guidewire.

20. The kit of claim 18, wherein the medical apparatus comprises a catheter.

21. The kit of claim 18, wherein the medical apparatus comprises a drill bit.

22. A method of manipulating a medical apparatus, the method comprising:

inserting the medical apparatus into a lumen of a patient's body; securing the torque device of claim 1 to the medical apparatus; and rotating the torque input member to thereby rotate the medical apparatus at a modulated speed.

23. The torque device of claim 17, wherein the lock system comprises a button operably coupled to the torque device such that upon depression of the button, contact between a portion of the button and a portion of the speed modulating system prevents rotation of the speed modulating system with respect to the button.

* * * * *